US009724023B2

(12) United States Patent
Swenson

(10) Patent No.: US 9,724,023 B2
(45) Date of Patent: Aug. 8, 2017

(54) WEARABLE METABOLIC PHYSICAL ACTIVITY MONITOR AND METHOD

(71) Applicant: Mission Biomedical Scientific, Inc., San Francisco, CA (US)

(72) Inventor: Francis Joseph Swenson, San Francisco, CA (US)

(73) Assignee: Mission Biomedical Scientific, Inc., San Francisco, CA (US)

( * ) Notice: Subject to any disclaimer, the term of this patent is extended or adjusted under 35 U.S.C. 154(b) by 16 days.

(21) Appl. No.: 14/676,983

(22) Filed: Apr. 2, 2015

(65) Prior Publication Data

US 2015/0289790 A1    Oct. 15, 2015

Related U.S. Application Data

(60) Provisional application No. 61/978,134, filed on Apr. 10, 2014.

(51) Int. Cl.
  *A61B 5/1455* (2006.01)
  *A61B 5/145* (2006.01)
  *A61B 5/00* (2006.01)

(52) U.S. Cl.
  CPC ........ *A61B 5/14539* (2013.01); *A61B 5/1455* (2013.01); *A61B 5/14507* (2013.01);
  (Continued)

(58) Field of Classification Search
  CPC ......... A61B 5/681; A61B 5/688; A61B 5/145; A61B 5/1455; A61B 5/14551;
  (Continued)

(56) References Cited

U.S. PATENT DOCUMENTS

RE31,879 E * 5/1985 Lubbers ............... G01N 21/643
                                                          422/562
8,849,697 B2 * 9/2014 Tropper ............. A61B 5/14539
                                                          600/300
(Continued)

OTHER PUBLICATIONS

Swenson, Frank J., "Development and evaluation of optical sensors for the detection of bacteria", Sensors and Actuators B, 11 (1993), pp. 315-321.

(Continued)

*Primary Examiner* — Eric Winakur
*Assistant Examiner* — Chu Chaun (JJ) Liu
(74) *Attorney, Agent, or Firm* — Christopher Peil; Law Office of Christopher Peil

(57) ABSTRACT

A metabolic physical activity monitor measures metabolic analyte data using one or more wearable analyte sensors. The sensors may be incorporated into a self-contained device or communicatively coupled to an external computing device like a smartphone or computer or both. Sensors may be mounted on any body surface including the skin, under the eyelid or in the mouth. Metabolic Analyte biomarker data may include electrolytes, various metabolites, $pCO_2$ and $pO_2$ in sweat, saliva and tears. Sensor data are used to calculate specific biomarker values, including calorie expenditure. Sensor readings are taken for at least two points during a period of physical activity. Changes in readings are used to determine total and rate of caloric expenditure for the time period. Readings may also be used to evaluate a user's wellness. By using measured changes in relative values complex calibration procedures can be eliminated, while reproducibility is much more easily achieved.

11 Claims, 6 Drawing Sheets

(52) U.S. Cl.
 CPC ...... *A61B 5/14517* (2013.01); *A61B 5/14546* (2013.01); *A61B 5/4866* (2013.01); *A61B 5/681* (2013.01); *A61B 5/688* (2013.01); *A61B 5/0002* (2013.01)

(58) Field of Classification Search
 CPC ............ A61B 5/14507; A61B 5/14517; A61B 5/14542; A61B 5/14539
 USPC ....... 600/300, 301, 345, 346, 348, 353, 367, 600/476
 See application file for complete search history.

(56) References Cited

U.S. PATENT DOCUMENTS

| | | | | |
|---|---|---|---|---|
| 9,131,893 | B2* | 9/2015 | Faybishenko | A61B 5/14507 |
| 2004/0242976 | A1* | 12/2004 | Abreu | A61B 5/0008 600/315 |
| 2012/0271121 | A1* | 10/2012 | Della Torre | A61B 5/024 600/301 |
| 2012/0323807 | A1* | 12/2012 | Sabeta | G06Q 30/02 705/317 |
| 2015/0359458 | A1* | 12/2015 | Erickson | A61B 5/14507 455/557 |

OTHER PUBLICATIONS

Andre, et al., "Recent Advances in Free-Living Physical Activity Monitoring: A Review", Journal of Diabetes Science and Technology, vol. 1, Issue 5, Sep. 2007, 8 pages.

Chang, Byoung-Yong, "Smartphone-based Chemistry Instrumentation: Digitization of Colorimetric Measurements", Bull. Korean Chem. Soc. 2012, vol. 33, No. 2, 4 pages.

Namazi, et al., "Can Proton Pump Inhibitors Accentuate Skin Aging?", Archives of Medical Research, vol. 41, Issue 2, pp. 147-148, Published Mar. 29, 2010, 2 pages.

Tusa, et al., "Optodes fluorescentes pour analytes de l'urgence", Annales de Biologie Clinique, vol. 61, No. 2, 183-91, Mar.-Apr. 2003, 5 pages.

Schmid-Wendtner, et al., "The pH of the Skin Surface and Its Impact on the Barrier Function", Skin Pharmacol Physiol 2006; 19:296-302, Published online: Jul. 19, 2006, 7 pages.

Kelly, et al., "Agreement between arterial and transcutaneous PCO2 in patients undergoing non-invasive ventilation", Respiratory Medicine (2011) 105, 226-229, Published online on Dec. 4, 2010, 4 pages.

"Sodium Bicarbonate Chemistry", IBT Bulletin, Integrated Biomedical Technology, Inc., 2003, 2 pages.

\* cited by examiner

WEARABLE METABOLIC PHYSICAL ACTIVITY MONITOR AND METHOD

CROSS REFERENCE TO RELATED APPLICATIONS

This application claims benefit of U.S. provisional patent application Ser. No. 61/978,134, filed Apr. 10, 2014, the entirety of which is incorporated herein by this reference thereto.

BACKGROUND

Technical Field

The present disclosure relates generally to detecting and measuring physical activity. More particularly, the present disclosure relates to a wearable metabolic physical activity monitor and associated methods.

Background Information

Obesity resulting in coronary heart disease and type 2 diabetes is a serious epidemic threat to the health of the population in almost every country of the world. Despite the genetic susceptibility of some individuals, the principal reasons for these medical problems are the unhealthy diets and sedentary lifestyles of the population at large. National campaigns educating the population of the risk factors and the need for a healthy diet and exercise are a high priority but, as yet, have not had a meaningful impact on obesity related disease. Education about healthy diets and monitoring food-calorie intake has been promoted by many private and government entities. In fact, food product labeling is mandatory in the United States and Europe and is increasingly being implemented in Asia and Latin America. Furthermore, health-conscious public and private organizations have recommended physical exercise, in addition to a healthy diet, as being critical for weight control programs. Unfortunately numerous profit-motivated organizations, both well-meaning and dubious, have promoted questionable rapid weight loss programs, unsubstantiated supplements and similar fad weight-loss programs.

Making healthier diet choices has met with some success, but the adoption of physical exercise on a routine basis has proved to be more challenging. Daily physical activity is essential to defeating obesity related diseases but weight loss programs fall short in persuading people to adopt a consistent physical exercise program. A major reason for such failures is that individuals are not able to track their efforts and receive immediate feedback. As a result, many computer and smart phone software programs have appeared that allow the user to track their food intake and calorie expenditure during exercise. Many individuals have found this to be a successful strategy for losing and maintaining weight. However, there are serious shortcomings to using this strategy for tracking calorie expenditure.

These include the inconvenience of manually keying in information for each individual physical activity and more importantly, the inherent inaccuracies of using generalized look-up lists of calorie expenditure values. The lists are based on estimates of an average person doing that activity. In actuality, there is so much variation between people that actual values for individuals are often vastly different when compared to the lists.

Personal wearable fitness monitors including wristbands, watches and even clothing have recently been introduced in an attempt to individualize and provide better calorie expenditure estimates. They add convenience because the monitors may include their own electronics, display and wireless connectivity and have the ability to connect to a smart phone or other computing device, allowing calorie expenditure to be calculated and recorded automatically. Fitness monitoring devices usually track movement with some type of movement instrument such as an accelerometer. Although accelerometer or similar instruments are fairly accurate when monitoring walking, running or sleeping, they are notoriously inaccurate when quantifying movement with other popular exercises. For example, racquet sports, skiing, yoga, weight lifting, tai chi and aerobics create various movement signals from the accelerometer but expended calorie values are unreliable because the device readings are calibrated to walking/running. Also, readings with accelerometer based fitness monitors are highly variable, even when measuring the same exercise activity, because readings depend both on the user's individualities and the physical placement of the device.

Typically monitors often use accelerometers or magnetometers attached or incorporated into a variety of wristbands, wrist and other watches, ankle bracelets or chest bands. The expended calories value is based on the accelerometer readings, together with providing the individual's age and weight. Thus, calorie expenditure values are commonly calculated for an average person of a certain gender, weight and height. For this reason, they are not actual values for a specific person but an estimate based, at best, on limited population studies (usually in Western Countries).

In reality, a large number of individual variables may influence the true expended-calorie value for a given exercise physical activity for a specific person. An individual's genetic makeup, BMI (body mass index), body composition, diet, medications and ingested supplements together with their underlying BMR (basal metabolic rate) all contribute to the number of calories being expended. Many devices use estimates of these values based on the average person. Assumptions are inaccurate for individuals in many cases. Although walking and running calorie expenditure may be approximated with accelerometer-based monitors, the same is not true for other physical activities depending on the type of exercise and body placement of the accelerometer. Because calorie expenditure is so individualized, the assumptions underlying the calculations based on accelerometer readings are valid for only a limited segment of the population.

SUMMARY

Figure 1:
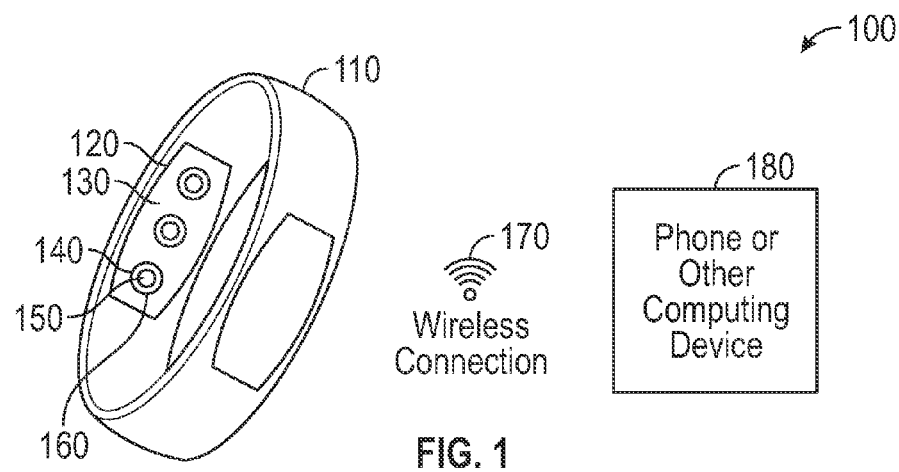
FIG. 1 shows a diagram of metabolic physical activity monitor system that includes a metabolic physical activity monitor communicatively coupled to a computational device such as a smartphone.

A metabolic physical activity monitor measures metabolic analyte data using one or more wearable analyte sensors. The sensors may be incorporated into a self-contained device or communicatively coupled to an external computing device like a smartphone or computer or both. Sensors may be mounted on any body surface including the skin, under the eyelid or in the mouth. Metabolic analyte biomarker data may include electrolytes, various metabolites, pCO2 and pO2 in sweat, saliva and tears. Sensor data are used to calculate specific biomarker values, including calorie expenditure. Sensor readings are taken for at least two points during a period of physical activity. Changes in readings are used to determine total and rate of caloric expenditure for the time period. Readings may also be used to evaluate a user's wellness. By using measured changes in relative values complex calibration procedures can be minimized, while reproducibility is much more easily achieved.

DETAILED DESCRIPTION

A metabolic physical activity monitor measures metabolic analyte data using one or more wearable analyte sensors. The sensors may be incorporated into a self-contained device or communicatively coupled to an external computing device like a smartphone or computer or both. Sensors may be mounted on any body surface including the skin, under the eyelid or in the mouth. Metabolic analyte biomarker data may include electrolytes, various metabolites, pCO2 and pO2 in sweat, saliva and tears. Sensor data are used to calculate specific biomarker values, including calorie expenditure. Sensor readings are taken for at least two points during a period of physical activity. Changes in readings are used to determine total and rate of caloric expenditure for the time period. Readings may also be used to evaluate a user's wellness. By using measured changes in relative values complex calibration procedures can be minimized, while reproducibility is much more easily achieved.

In view of the needs unmet by the current state of the art, described herein above in the Background, there exists a need for a physical activity monitor that more accurately tracks the true number of calories being expended during all physical activities and reflects the contribution of all of the individual's unique factors.

A system as described herein is capable of measuring metabolites that result from the catabolism of carbohydrates, fat and protein and which therefore correlate strongly to actual calorie expenditure, allowing an estimate of calorie expenditure that more closely approximates the actual calorie expenditure.

Metabolic biomarker data are measured using underlying sensor technology that has been well documented in the scientific and medical literature. Sensors developed for measuring pCO2, pO2 and multiple other analytes have been available commercially for 30 years. These sensors are scientifically and medically validated primarily for measurements in blood as medical devices. They are available in a number of configurations and are based on well-established optical-chemical or electrochemical principles. Analyte sensors can be single-use, or multi-use. Documented, verified and validated manufacturing procedures are available for commercially available sensors. Sensors for determining analyte values in blood samples have been proven to be accurate and reproducible. In clinical use, it is imperative that these sensors determine absolute numerical values for blood analyte concentration that enable a physician to properly guide treatment. Multiple clinical studies have verified the accuracy and precision of blood values obtained by approved sensor based devices.

However, the same is not true when measuring analyte concentration in body fluids other than blood. Known problems include reproducibility, difficulties with sensor calibration and an inability to predict blood levels based on analyte concentrations in body fluids other than blood.

Applicant has discovered that the foregoing issues associated with analyte determination in body fluids other than blood are not problematic in the use of a metabolic physical activity monitor as described herein. Applicant has further discovered that absolute measurements of analyte level are not critical when measuring the physical activity, health and wellness status of an individual. The sensors used herein need only measure a change from baseline and prior readings. Such signal changes (positive or negative) are recorded and evaluated as relative changes over time, which result from a specific individual performing any activity.

Values are used in an algorithm to calculate specific biomarker values, including calorie expenditure. Using relative values rather than absolute numbers has several other advantages: enhancing the robustness of the system by removing difficult calibration procedures and relaxing constraints on manufacturing specifications for the sensor baseline readings. As a result, monitors using the present system are more accurate, versatile and less expensive to manufacture. As a result the monitor can provide a measurement of changes in calorie expenditure that;

is a direct reflection of metabolic activity as it relates to activity level; and is more personalized to the individual.

Thus, a metabolic physical activity monitor, as described herein, measures metabolites that result from the catabolism of carbohydrates, fat and protein and therefore represents a genuine direct measure of calorie expenditure.

FIG. 1 shows a metabolic physical activity monitor system 100 that may include one or more wearable physical activity monitors 110 communicatively coupled to a computational device such as a microprocessor, smartphone, smart display or watch 180. In an embodiment, concentrations of metabolic analyte biomarkers are measured using a plurality of metabolic sensors 140 in firm contact with a surface of the body of a user to obtain readings from the skin, or other surfaces, sweat, tears and/or saliva of an individual. Changes in the metabolic sensors 140 may be detected using transceiver devices, such as a LED and Photodiode combination devices. The light transceiver module may contain a base 130, at least one light-emitting device for providing optical signals 150, at least one light-receiving device 160 for receiving optical signals, and a main circuit board 130. The light emitting device 150 and light receiving device 160 may utilize optical filters or similar methods to select specific light wavelengths. The base (130) supports a plurality of light transceiver modules (140) that correspond to placement of the metabolic sensors (120). The base (130) may have other electronic components including a power source, A/D converters, electric connectors and direct or wireless communication (170) for connections with the computing device. In some configurations described herein it may be necessary to use extremely small and light electronic components perhaps down to the nanoscale.

Figure 2:
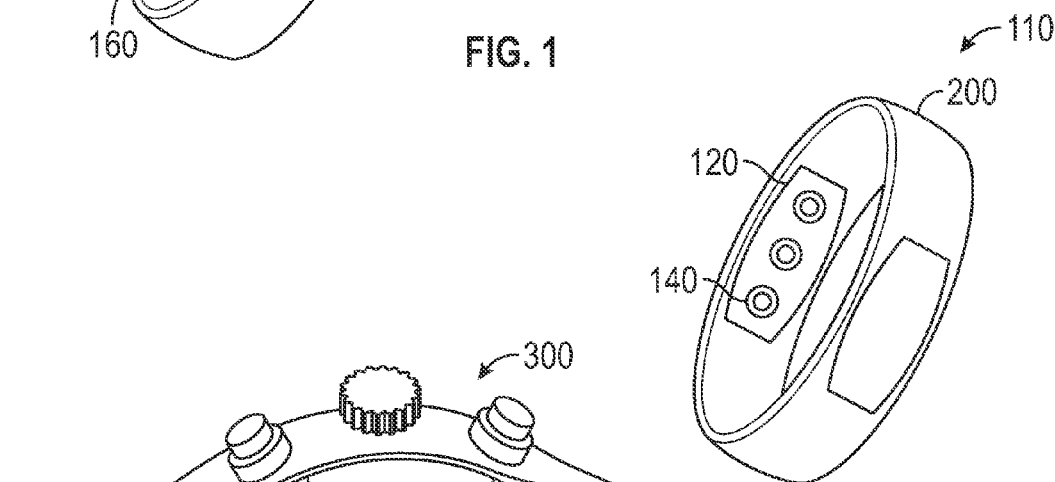
FIG. 2 shows an example of a metabolic physical activity monitor that includes a wristband monitor.
Figure 3:
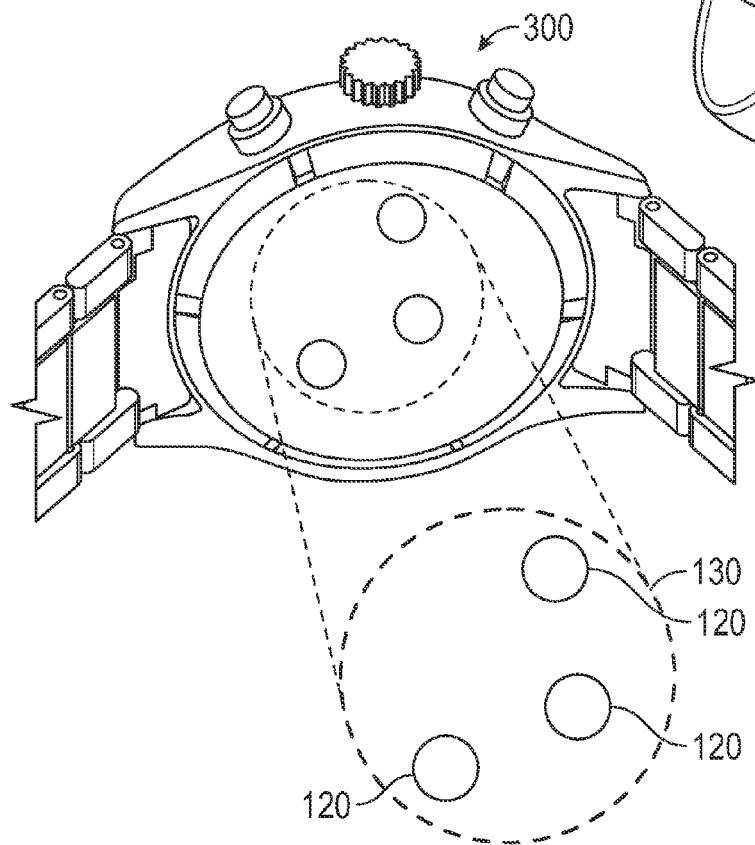
FIG. 3 shows an example of a metabolic physical activity monitor that includes a watch.

FIGS. 2 and 3 show examples of a metabolic physical activity monitor 120 that include wristband devices 200, and 300. Multiple configurations are possible, including a tight-fitting bracelet 200 or watch 300 incorporating at least one removable sensor element, patch or cartridge 120. The wristband device may utilize one or more separate sensor elements 120 having different sensing capabilities. The changes in the metabolic sensors 120 are monitored by being placed in close contact to the light transceiver devices (140) incorporated into the wristband devices 200, 300. When worn, the sensing elements 120 may adhere directly to the skin, directly to the wristband device or may be held in firm contact with the skin of the individual by the wristband device. The other electronic components as described in FIG. 1 are incorporated into the wristband device. In embodiments, the wristband may be adjustable to accommodate a variety of wrist/arm sizes. Readings from the skin and sweat may be analyzed using a plurality of sensors, each providing metabolic information, about the individual. In further embodiments, the sensing elements may be held in secure contact with the skin by various securing mechanisms, including, for example, ankle bracelets, skin patches, chest bands, necklace bands and special clothing. The metabolic data are used to assess the fitness and health of the individual, including calorie expenditure.

Figure 4:
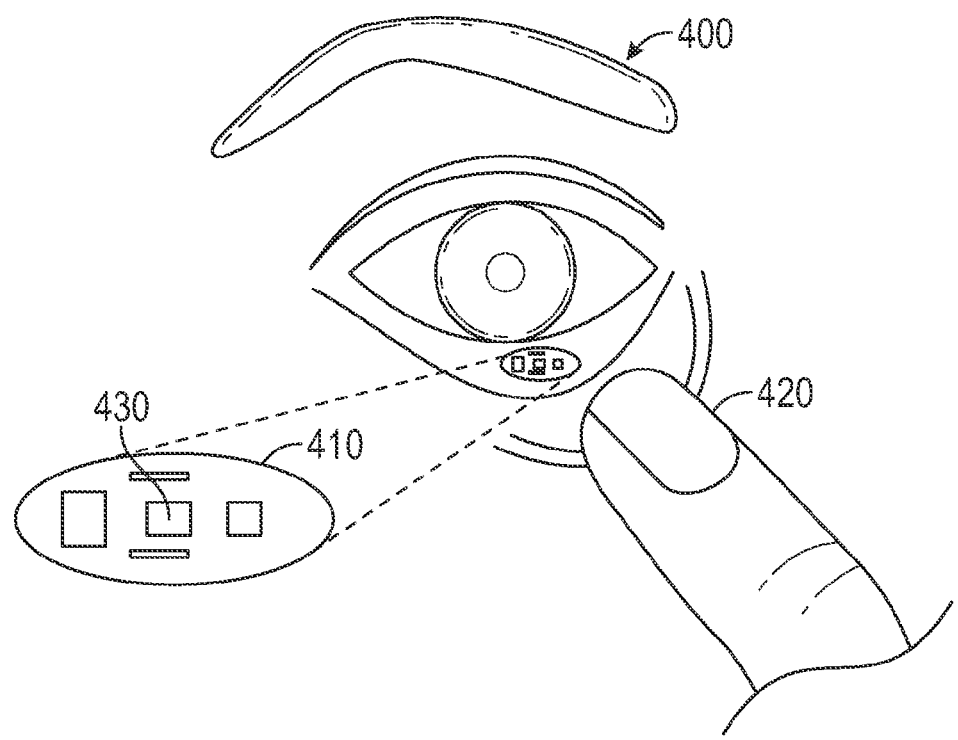
FIG. 4 shows an example of a metabolic physical activity monitor wherein one or more sensors are used to obtain readings from the conjunctiva and tears of a user.

Referring now to FIG. 4, shown is an embodiment 400 wherein one or more sensors are used to obtain readings from the conjunctiva and tears of an individual. One or more ocular sensor cartridge inserts 410 may be placed 420 under an eyelid 420 and may then be used to determine levels of metabolic analytes on the conjunctiva, the inner surface of the eyelids and in the tears.

In an embodiment, sensors may be embedded in a flexible matrix, similar to a soft contact lens, which is compatible with eye and skin. Embodiments may be fabricated, for example, from silicone or hydrogel polymers, such as those used to make soft contact lenses.

Advantages of an ocular insert 410 may include that it is easy to insert, comfortable, does not compromise the cornea and does not interfere with vision. In use, the insert may be placed under either eyelid and may even be a ring structure that allows it to be positioned under both the upper and lower eyelid without touching the cornea. Other examples of an ocularly-inserted sensor cartridge may include punctal inserts and contact lenses.

Figure 5:
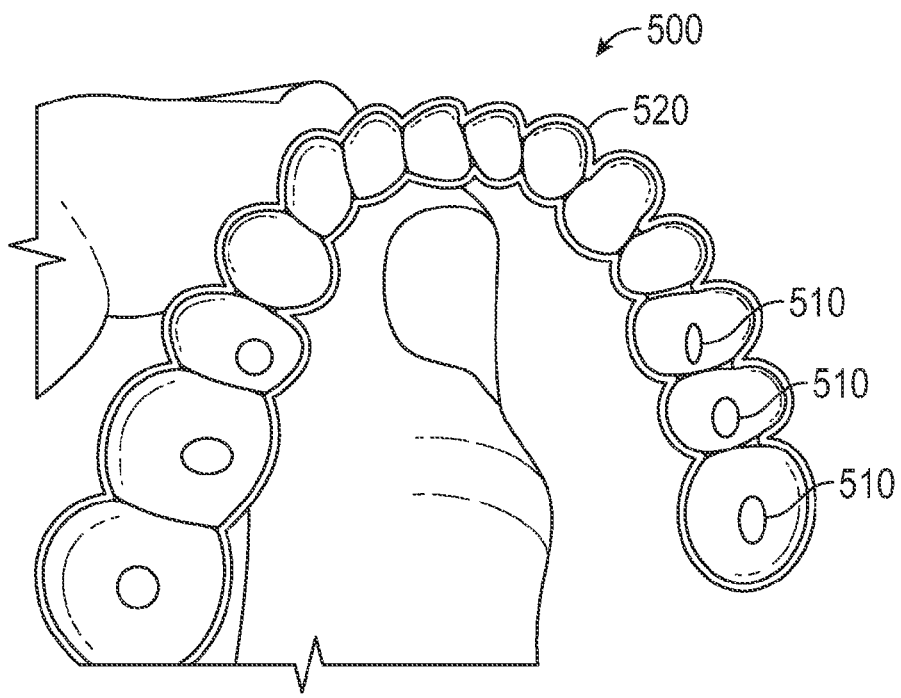
FIG. 5 shows an example of a metabolic physical activity monitor that includes an oral insert wherein sensors are used to measure the levels of metabolic analyte biomarkers on the gums and in the saliva.

In embodiments, sensors may alternatively or additionally be used to obtain readings from the gums and saliva of an individual. FIG. 5 shows an embodiment 500 wherein sensors 510 are used to measure the levels of metabolic analyte biomarkers on the gums and in the saliva using an oral insert 520 equipped with one or more sensors 510.

The sensors used in the embodiments described herein are those that provide useful information in a chosen body location about the fitness and calorie expenditure of the user, including measurements of acidity/alkalinity (pH), partial pressure of oxygen (pO2,) partial pressure of carbon dioxide (pCO2), saturated oxygen (sO2), electrolytes (including $Na^+$, $K^+$, $Ca^{++}$, $Cl^-$), urea, lactic acid, temperature, humidity and glucose. The sensors embody a number of well-established scientific principles including electrochemical and optical mechanisms.

In an embodiment, the metabolic physical activity monitor may constitute a disposable device that incorporates a plurality of metabolic sensors that are applied to a body surface, such as the skin, inner eyelid or the inner surface of the lip. In an embodiment, the sensors react to changes in the level of one or more selected metabolites in one or more of sweat, tears, or saliva over the activity monitoring period. In embodiments, the monitoring period may vary from 1-48 hours, depending on the analyte being measured, the sensor type and the type of activity.

Periodic monitoring may be done in situ or at the end of the monitoring period. Readings may be made using a dedicated reading device, a modified existing fitness monitor or watch, a smartphone camera or even by visible comparison to a reference chart.

A single-use embodiment may include a plurality of metabolic sensors for application to a body surface such as the skin. The sensors may react to changes in the level of one or more selected metabolites in one or more of sweat, tears, or saliva over the activity monitoring period.

An embodiment may include measuring levels of metabolic analytes with sensors as described herein above, and using data regarding metabolic analyte level in conjunction with other physiological data to provide a more comprehensive and useful measure of the physical activity, health and wellness status of an individual. Such other physiological data may include age, gender, body weight, heart or pulse rate, body or skin temperature, blood pressure and optically-determined blood oxygen saturation, often known as pulse oximetry.

Description of Analyte Sensors

Sweat is predominantly water but contains many major constituents including Na+, K+, CL−, Lactate, HCO3 and several minor constituents like urea, fatty acids, proteins, glucose, pCO2 and pO2. For the most part, sweat constituents originate from the blood but do not occur in sweat at the same levels or the same relative proportions as in the blood. Nevertheless, there have been many studies that have attempted to deduce analyte blood levels based on skin and sweat measurements. For the most part, the degree of correlation and reproducibility has not been adequate for use as a substitute for laboratory blood measurements. (Kelly and Klim 2011) The present system discloses that the detection and measured change in metabolic analytes in skin and sweat will provide a better measure of caloric expenditure than conventional wearable fitness monitors.

Analyte measurements in sweat that best reflect metabolic changes are pCO2, and pH. In addition pO2, free fatty acids, lactate and urea may also be useful.

Several proof of concept experiments were performed. To demonstrate the concept, sensors were used to measure the skin/sweat levels of pCO2 and pH.

Carbon Dioxide

CO2 was chosen because carbon dioxide is a universal by-product of substrate aerobic catabolism. While most CO2 is expired in the lungs as a gas, a small but significant amount is emitted through the skin from the blood and equilibrates with the surface sweat (pCO2).

Carbon Dioxide (CO2 Physiology)

Figure 6:
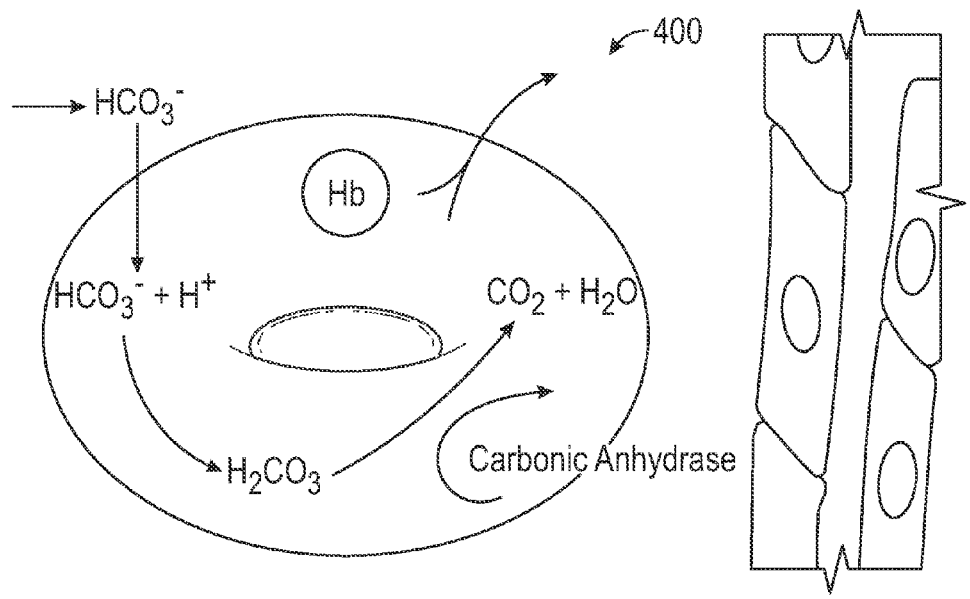
FIG. 6 shows a diagram of $CO_2$ physiology in the lungs.
Figure 7:
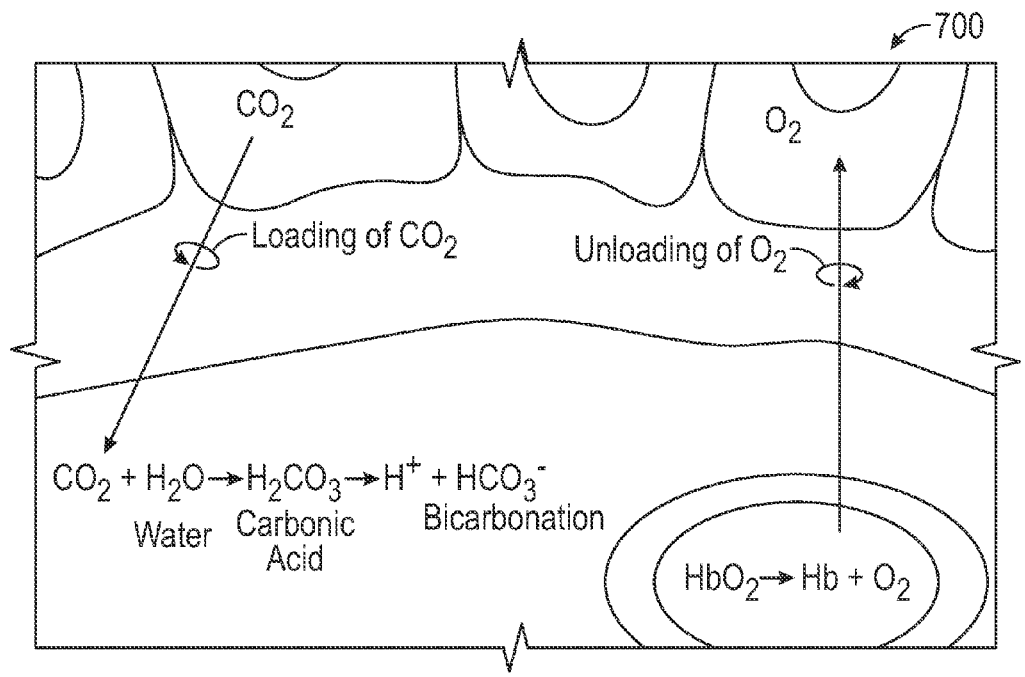
FIG. 7 shows a diagram of $CO_2$ physiology in somatic tissue.

Referring now to FIGS. 6 and 7, shown are diagrams depicting CO2 physiology in the lungs 600 and blood 700.

Referring first to FIG. 6, in a fit, healthy person:
Between 5 to 8 liters of air per minute are exchanged in the lungs where there is an exchange of oxygen and carbon dioxide;
At rest, approximately 300 ml per minute of O2 is transferred through the alveoli to blood while a similar volume of CO2 is transferred to the lungs and exhaled;
During exercise, up to 100 liters of air per minute can be exchanged allowing 3 liters of oxygen per minute to be extracted and a similar volume of CO2 exhaled;
The rate at which O2 is used and CO2 produced by the body are both measures of the rate of energy expended by the body (calorie expenditure).
Referring next to FIG. 7:
CO2 is carried in blood plasma as bicarbonate. About 98% (+−1%) of it is eliminated through the lungs. The remainder is lost through the skin;
As the skin temperature increases more CO2 is lost through the skin.

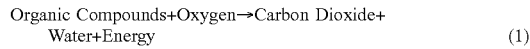

$$\text{Organic Compounds} + \text{Oxygen} \rightarrow \text{Carbon Dioxide} + \text{Water} + \text{Energy} \quad (1)$$

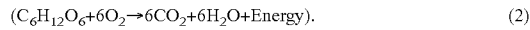

$$(C_6H_{12}O_6 + 6O_2 \rightarrow 6CO_2 + 6H_2O + \text{Energy}). \quad (2)$$

Transcutaneous (TC) CO2 monitors have been developed as medical devices to provide a semi-continuous estimation (PtCO2) of arterial pCO2 in patients.

TC CO2 monitors have proved useful in neonatal monitoring where drastic pCO2 changes can be detected.

TC CO2 monitors are not considered accurate enough for determining true pCO2 (arterial levels) to be used in adult patients. Numerous investigators concluded TC was not sufficiently accurate to replace Arterial Blood Gas measurements.

In addition, CO2 is also produced by skin cells and contributes to the levels of pCO2 in sweat. Calorie expenditure is already an important measure for several medical situations. A number of medical validated methods exist that measure carbon dioxide in expired breath.

For example, a Metabolic Cart utilizes indirect calorimetry and measures the levels of O2 and CO2 exhaled by a patient. The O2 and CO2 values are used to calculate calorie expenditure under laboratory conditions. (Frankenfield et al, 2008). Another clinical laboratory method for measuring calorie expenditure is the Double Labeled Water Isotope procedure. It is based on the patient drinking a solution containing isotopes of hydrogen and oxygen. Tests for these isotopes are performed on saliva and urine as these isotopes are eliminated from the body over 1-2 weeks. Baseline readings are taken and follow up readings taken 7-14 days later. Comparing the difference between the rate of elimination of the two isotopes allow the rate of CO2 to be calculated as a measure of calorie expenditure. These laboratory based measures of calorie expenditure are accurate but very expensive, complicated and totally impractical for use outside of a laboratory setting.

As described above, measuring the rate of CO2 production is indicative of calorie expenditure. The present system discloses a simpler, responsive, inexpensive alternative to previous methods. Measuring pCO2 on skin has been described in a small number of publications. These studies were attempts to provide an alternative to the invasive, arterial blood methods that are routinely used in hospitals to determine blood gas values. Commercial clinical laboratory instruments for measuring blood gases, including pCO2 and pH have been available for decades from medical companies like IDEXX, SIEMENS, MEDICA and RADIOMETER. Both electrochemical and optical measurements were used to determine blood gas values as well as levels of other blood analytes.

Transcutaneous studies (skin and sweat) that included pCO2 measurements used medical devices that were more complicated and expensive than the present system. For example, they included components for heating the skin to promote gas release from the skin. Additionally, they required high levels of standardization between electronics and sensors. Although there was mixed success for determining values in newborn infants, investigators found transcutaneous readings too inaccurate and irreproducible for clinical use. (Kelly and Klim 2011).

The system described herein provides the capability of measuring carbon dioxide levels but does not present the problems of the transcutaneous methods described above. Whereas the clinical studies were attempting to determine absolute arterial blood values for blood gases by measuring skin and sweat, the present system is concerned with determining the rate of change in pCO2 signal in sweat and skin. Because actual analyte values are not calculated, the signal change that occurs due to the increase in pCO2 from a base level and over a measured time, the relative change in the pCO2 signal, is used to determine the caloric expenditure. The increase in pCO2 signal is due not only to the CO2 being released from the blood. The skin cells additionally increase their output of CO2 as a result of the increased activity of sweat glands. Moreover, during exercise the skin increases in temperature, which also promotes the release of CO2, allowing more gas to interact with the sensing element of the device. Also, increased acidity occurs in exercise-induced sweat (see below), which also drives the gaseous form of CO2 (IBT bulletin).

Methodologies for measuring pCO2 and CO2 are well described in thousands of publications and include optical (including reflectance, absorbance, fluorescence, or chemiluminescence methods), electrochemical, amperometric, potentiometric, electronic, and spectrophotometric (using visible, near infrared or infrared wavelengths). Any method is consistent with the present system, providing that sensors and methodologies are prepared in a defined, consistent manner and calibrated to achieve the appropriate signal range and response time.

A second analyte measurement, pH, was investigated to determine whether sweat acidity increased during exercise and could be used as a metabolic indicator of caloric expenditure. The skin has an "acid mantle" with a pH of approximately 5.5. The acid mantle provides barrier properties, selective penetration properties and an antimicrobial layer that lowers the risk of infection. The acid mantle is also apparently necessary for certain enzymatic activities, such as healing, that occur at or just beneath the skin's surface (Schmid-Wendtner and Korting 2006). The origin of the acid mantle is not really known but it is suspected that it is a combination of lactic acid, free fatty acids from hydrolysis of phospholipids in skin gland secretions and the results of active proton pumps in the skin. Although, information on skin proton pumps is limited, there is evidence that proton pump inhibitors, often given as a treatment for gastroesophageal disease (GERD), may cause skin problems (Namazi and Jowkar 2010). Our initial experiments indicated that during prolonged exercise the sweat pH dropped significantly below 5.5 and returned quickly to 5.5 after the cessation of physical exercise.

The exact explanation for this drop in pH is not known, but it is likely a result of a combination of factors including increased free fatty acid deposition from sweat, increased proton pump activity in the skin, and increased carbonic acid and lactic acid production. In any case, the pH decrease is in response to physical activity and it does correlate to caloric expenditure.

Methodologies for measuring pH are well described in thousands of publications and include optical (including reflectance, absorbance, or fluorescence, or chemiluminescence methods), electrochemical (amperometric, potentiometric). Any method is consistent with the present system, providing sensors and methodologies are prepared in a defined, consistent manner and calibrated to achieve the appropriate signal range and response time.

Proof of Concept—Carbon Dioxide and pH Sensor

For proof of the concept underlying the present system, two analytes were measured to demonstrate that the changes in the analytes were correlated to caloric expenditure. For these experiments, two types of optical absorbance sensor methods were employed to measure (1) CO2 production and (2) increased sweat acidity. Multiple experiments were performed with the following protocol.

The following stock buffer solution was prepared using conventional laboratory procedures:

Carbonate-Bicarbonate Buffer Ingredients:
- A. Sodium carbonate solution 0.2M: Dissolve 2.12 gm of anhydrous sodium carbonate in 100 ml Distilled water;
- B. Sodium bicarbonate solution: Dissolve 1.68 gm of sodium bicarbonate in 100 ml of distilled water; and
- C. 1N HCL and 5N NaOH to adjust pH.

Procedure:

Stock Buffer

Transfer 27.5 ml of sodium carbonate (solution A) to 22.5 ml of sodium bicarbonate solution (Solution B). Adjust to 100 ml with distilled water and adjust pH to 10 with solution C.

pCO2 Sensor
- Indicator solution—Universal pH indicator* (tested various concentrations 0.04%-0.4%) dissolved and tested in various dilutions of STOCK BUFFER (0.002-0.2M);
- GE 11 Silicone (GENERAL ELECTRIC CORPORATION, Fairfield Conn.)—Neutral, clear.

Mix silicone with Indicator solution using wood applicator. Use enough indicator solution to be slightly in excess of that amount that can be completely absorbed by the silicone. Continue mixing until uniform. Spread mixed silicone on a flat surface, remove excess solution and allow to cure at room temperature (RT) for 24 hours. Use a standard hole punch to produce sensor discs.

pH Sensor

Use universal* pH paper and cut into 50 mm squares. For testing, adjust pH on squares to various pH starting points (pH 12-4) using STOCK BUFFER. Allow to dry at RT for 24 hours on absorbent filter paper.

Using/Testing Sensors

Place test sensors on Subject's arm and hold in place using SCOTCH brand (3M CORPORATION, St. Paul, Minn.) book tape.

Universal indicator includes water, propan-1-ol, phenolphthalein sodium salt, sodium hydroxide, methyl red, bromothymol blue monosodium salt, and thymol blue monosodium salt.

Testing Protocol
1. Test subjects were fitted with sensors and were required to exercise on an elliptical or treadmill from 60-180 min. The elliptical and treadmill display readings (adjusted for weight and age of the subject) were used to measure caloric expenditure;
2. Using a smartphone (IPhone 5s) photos of the sensors were taken at the start and approximately at 15-30 min intervals;
3. Photos were corrected for white balance and displayed on a desktop Apple MAC using iPhoto. RGB values for sensor images on screen were measured using an iPhone App (COLORIMETER, WIAPPS, Berlin, Germany);
4. RGB values were converted to hue values according to the protocol described by Chang 2012. Hue values were then plotted against the calories expended as determined by the elliptical or treadmill.

Results

Multiple experiments were performed over 3 months on 2 different subjects. Typical Results are shown in FIGS. 8-10.

Figure 8:
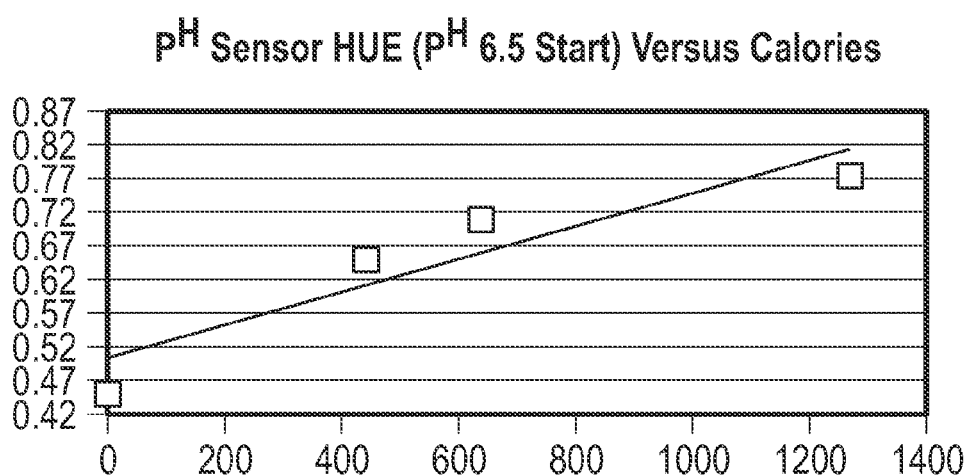
FIG. 8 shows a graph demonstrating the relationship of caloric expenditure with change in the pH sensor prepared at pH 6.5.
Figure 9:
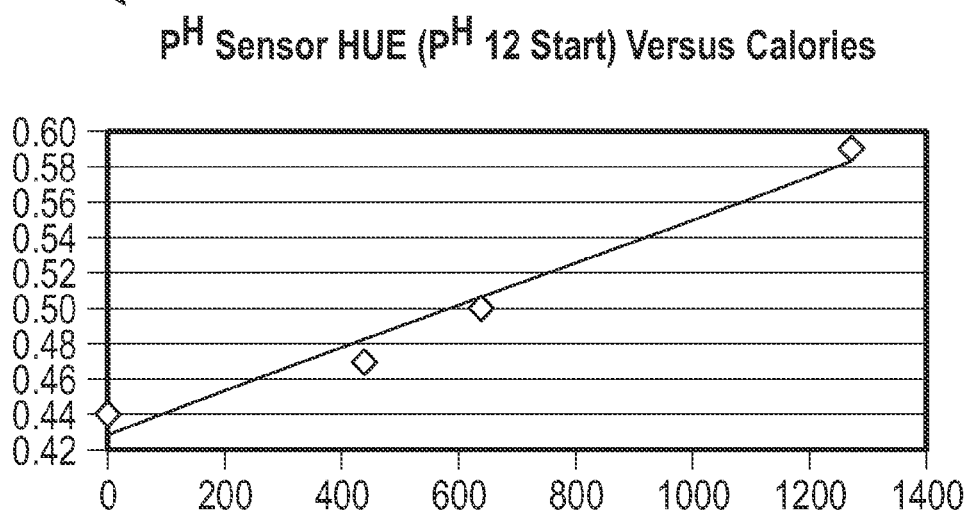
FIG. 9 shows a graph demonstrating the relationship of caloric expenditure with change in the pH sensor prepared at pH 12.
Figure 10:
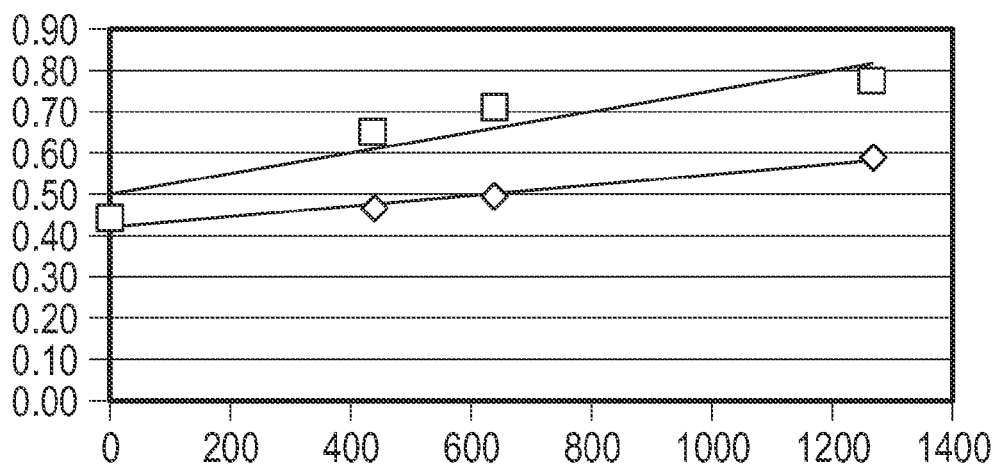
FIG. 10 shows a graph demonstrating the relationship of caloric expenditure with change in the pH sensor.

FIGS. 8-10 show examples of the results obtained with the pH sensor. Multiple experiments with different exercises (ellipse trainer, treadmill and hiking) on two individuals were done. In the experiments shown here two types of pH sensors with different baseline pH values were monitored while one participant used an ellipse trainer for 2.5 hours. The graph 800 in FIG. 8 shows the results when the pH of the sensor was adjusted to 6.5 as the start value. The graph 900 of FIG. 9, shows the results when the pH of the sensor was adjusted to 12 as the start value.

Although color changes could be seen visibly during the experiment, the methodology described above was used to generate digital optical readings. The horizontal axis of the chart describes the number of calories expended at time 0, time 30 min, time 60 min and time 120 min. The calorie expenditure value was obtained from the ellipse trainer's visual display (which was calibrated for the weight and age of the participant. The vertical axis is the calculated hue value determined by the method of Chang and directly correlates to pH values. In the top graph the universal indicator component of the sensor changed visibly from dark blue (pH 12) to mid green (pH 9). The hue value calculations were based mostly on an increase in green color. In the graph 1000 of FIG. 10, the universal indicator component of the sensor changed visibly from light green (pH 6.5) to mid orange (pH 9). The hue value calculations were based mostly on an increase in red color. In both pH graphs, there is an inverse relationship with hue values and pH value, so the increasing hue value with caloric expenditure indicates a pH decrease in the sweat/skin of the exercising participant.

Figure 11:
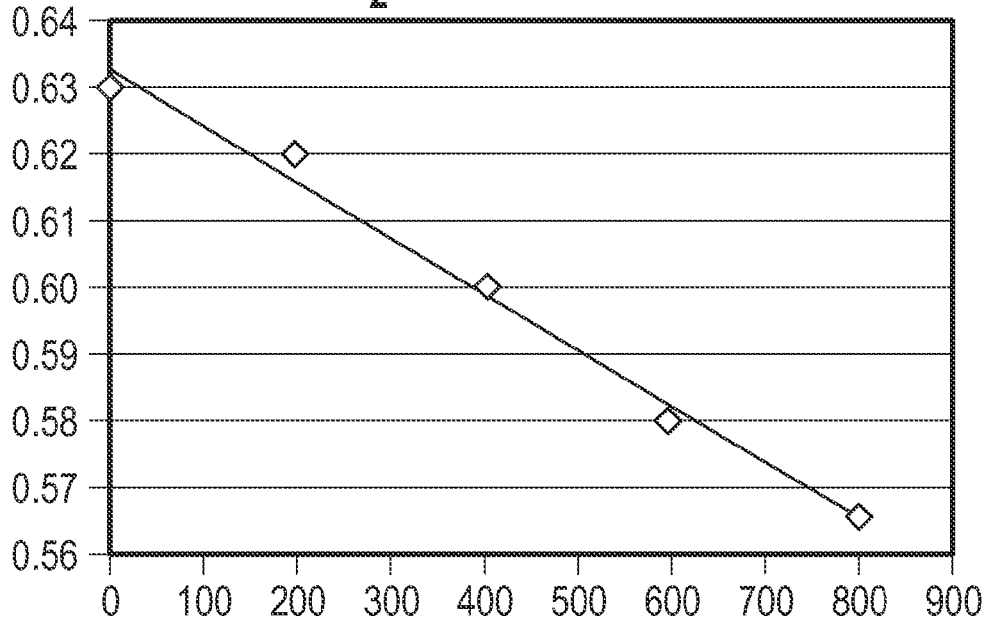
FIG. 11 shows a graph demonstrating the relationship of caloric expenditure with change in the pCO2 sensor.

FIG. 11 shows a graph 1100 of the results obtained with the pCO2 sensor. Multiple experiments with different exercises, for example, ellipse trainer, treadmill and hiking, on two individuals were done. In the experiments shown here, a pCO2 sensor prepared as described above was monitored on one participant using an ellipse trainer for 1.5 hours.

Although color changes were evident during the experiment, the methodology described above was used to generate digital optical readings. The horizontal axis of the chart describes the number of calories expended at time 0, time 15 min, time 30 min, 60 min and time 90 min. The caloric expenditure value was obtained from the ellipse trainer's visual display, which was calibrated for the weight and age of the participant. The vertical axis is the calculated hue value determined by the method of Chang and directly correlates to pCO2 values. The pCO2 sensor principle has been well described in a multitude of publications over the last 30 years.

The metabolic sensor prepared as described above relies on at least the following principles:

- $CO_2$ gas is liberated from the sweat as it becomes saturated with the $CO_2$ being produced by the physical exercise. $CO_2$ is also liberated from skin during exercise;
- The gaseous $CO_2$ passes through the water impermeable silicone barrier of the sensor and dissolves in the aqueous buffer solution within the sensor to form carbonic acid; and
- The dissolved universal indicator solution at pH 6 turns acidic and the sensor changes color from light green to yellow to orange (<pH 3).

In FIG. 11, hue value calculations were based on a change in green color hue. There is a direct relationship with hue values and pH value, so the decreasing hue value with caloric expenditure indicates a pH decrease in the sweat/skin of the exercising participant.

In an embodiment, a smart phone camera was used to capture and later analyze the results. While suitable for proof of concept experiments, in other embodiments, color changes of the metabolic sensor would be measured, analyzed and interpreted with greater accuracy and precision using a photometric reader, for example any of a colorimeter, fluorimeter, luminometer or chemiluminometer.

Analyte levels on the skin/sweat change as a result of an increase or decrease in physical activity. The invention described herein measures the change in the signal due to the analyte at regular intervals. Readings of the sensor output can increase or decrease with a change in the analyte concentration. However, each sensor is prepared and calibrated in a consistent manner so that the amount of change in signal is directly related to calorie expenditure. Different analytes require different sensors with different formulae for calculating calorie expenditure.

Caloric Expenditure

At a minimum, calorie expenditure readings may be calculated from the difference readings between the baseline and the end of a timed physical activity. In an embodiment, the readings may be taken more frequently, allowing the system to be more accurate and permitting a number of different physical activities to be measured during the same monitoring period.

Example: 3 Hour Physical Activity

Sensor Readings are measured at baseline and every 5 min until monitoring period ends Method:
Baseline Reading recorded.
Additional readings over 3 hours taken at 5 minute intervals.

Calorie Expenditure Calculations:
- Moving average Calorie expenditure rate (MACER) may be calculated using 2 previous readings (3 time points);
- If calorie expenditure rate is increasing or steady (within 10%), Total Calorie Expenditure (TCE) may be calculated, stored and displayed at each time point;
- If MACER drops below 10% of previous MACER, no additional TCE is added;
- When the MACER begins increasing again compared with previous MACER value. The first reading of this moving average is considered the new baseline and the calories expended is added to the TCE;
- The process may be continued until the monitoring period is completed; and
- The results from all sensors used during the activity are compared and the combined mean value may be displayed as the Final TCE.

Figure 12:
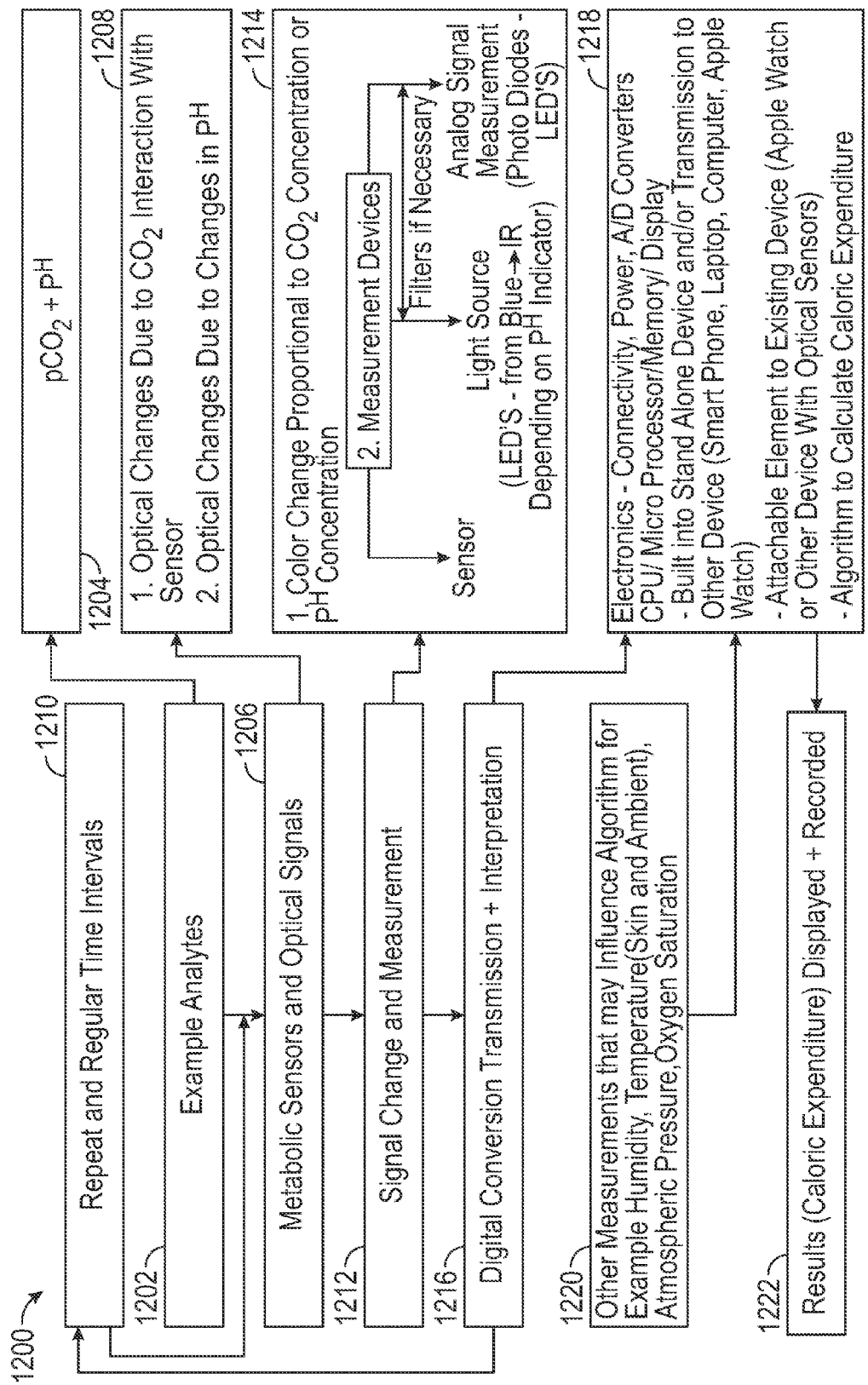
FIG. 12 shows a photometer with which one or more embodiments are realized.

An example of a colorimeter device for $pCO_2$ or pH is shown in FIG. 12. Optical signals may be digitally converted and analyzed using algorithms on a computing device (for example, a phone or a watch, but also a tablet, laptop or desktop computer) and the caloric expenditure determined. The connection between the computing device and the detection electronics may be wired or wireless (for example, BLUETOOTH: IEEE 802.11, 802.15.1, 802.15.4 and 802.15.6 wireless standards, which are hereby incorporated by reference in their entirety by this reference thereto).

As shown in FIG. 12, any of a number of target analytes found in various body fluids disposed on body surfaces 1202 may be analyzed by the device 1200. Metabolic degradation of the target analytes results in liberation of $CO_2$ and hydrogen ions. Measuring $pCO_2$ and pH 1204, concentration in the body fluid of any of the target analytes can be reliably inferred through the application of a calibration algorithm. A plurality of metabolic sensors gathers data regarding optical signals emitted at a measurement site 1206. The data regarding the emitted optical signals is representative of (1) optical changes due to $CO_2$ interactions with the sensor and (2) optical changes due to changes in pH 1208. Optical changes may be measured 1212 by the device 1200. In an embodiment, the optical changes may be one or both of: (1) color change proportional to $CO_2$ concentration and (2) a change in pH 1214. In embodiments, the measurement device may include at least one of:

- a power supply, such as a battery;
- a light source, such as one or more LEDs. In embodiments the color of the LEDs may emit in a range from blue to near IR depending on the type of indicator being measured; and
- one or more elements for analog signal measurement such as photodiodes or LEDs.

The device 1200 may further include, optical filters or similar method to select wavelengths of light, an element, such as an A/D convertor and a route of transmission 1216 for digitizing the measured signal and transmission to an analyzer.

The processes of signal detection and measurement may be repeated 1210 at regular time intervals.

In an embodiment, the analyzer 1228 may include any of:
- electronics for any of connectivity, power and A/D conversion and transmission to other devices;
- at least one of a processor, a memory and a display.

In embodiments, the analyzer may be a standalone device such as a smartphone, a laptop computer or an APPLE watch.

In embodiments, the foregoing elements can be integrated into an element that is attachable to another device, such as an APPLE watch that is equipped with optical sensors.

Further, the memory of the analyzer will have stored therein computer-readable code for carrying out an algorithm for calculating caloric expenditure from the measured optical changes.

Other measurements that may influence the algorithm and which may be measured include:
- humidity;
- skin temperature;
- ambient temperature;
- atmospheric pressure;
- and $O_2$ saturation.

Finally, a display 1222 will present the calculated value for caloric expenditure to the user.

Values may be stored and displayed as needed. These types of optical readers have been routinely used in several laboratory instruments for multiple types of assays (Swenson 1993, Tusa et al. 2002).

The results clearly demonstrate that pCO2 and pH values track caloric expenditure. Both pCO2 and pH are functions of physiological changes that result from the catabolism of organic substrates and are not subject to the susceptibility to artifacts that current wearable technologies use.

It is to be appreciated that, with appropriate validation and regulatory approval, wearable monitors, as described herein may be used as medical devices, for example, in the monitoring of patients having chronic diseases such as chronic pulmonary obstructive disease (COPD), Alzheimer's disease, and restless leg syndrome. Wearable monitors may also be used in clinical studies and trials for testing effects of new drugs and medical devices.

In the foregoing specification, the present system has been described with reference to specific exemplary embodiments thereof. It will, however, be evident that various modifications and changes may be made thereto without departing from the broader spirit and scope set forth in the appended claims. The specification and drawings are, accordingly, to be regarded in an illustrative sense rather than a restrictive sense.

The invention claimed is:

1. A metabolic physical activity monitor comprising:
    at least one water-impermeable, gas-permeable, chemically-reactive skin sensor having at least one surface that is configured to contact a measurement site on a body surface of a subject;
    said at least one water-impermeable, gas-permeable, chemically-reactive skin sensor comprising a chemical indicator that exhibits a predictable color responsive to a corresponding CO2 concentration at least in sweat emitted from the subject's skin at the measurement site;
    at least one light source for illuminating the measurement site;
    at least one image capturer for detecting light reflected by said at least one chemically-sensitive skin sensor;
    at least one signal transmitter that transmits detected light to an A/D convertor for conversion to digital data representative of the detected light;
    a processor;
    at least one memory device storing the digital data representative of the light given off by said at least one chemically-sensitive skin sensor stored therein;
    said at least one memory device further comprising previously-collected calibration data mapping hue values to caloric expenditure values;
    said at least one memory device further comprising computer program code for:
        extracting RGB values from said digital data representative of samples of light emitted by said at least one chemically-sensitive skin sensor;
        converting the extracted RGB values to hue values;
        obtaining a hue value for each of one light sample obtained at a first point in time and at least one light sample obtained at a second point in time;
        determining caloric expenditure values on said data by mapping hue values to caloric expenditure values;
        comparing the caloric expenditure values for a time period defined by said first point in time and said second point in time and determining a caloric expenditure for the time period; and
        outputting the caloric expenditure for the time period, wherein the calorie expenditure is an indicator of a subject's physical activity.

2. The metabolic physical activity monitor of claim 1, further comprising a body-worn base, configured for:
    mounting at a body surface;
    receiving the at least one sensor; and
    maintaining close contact between the at least one sensor and the measurement site during use.

3. The metabolic physical activity monitor of claim 2, wherein the body-worn base comprises at least one of:
    a piece of tape;
    a wristwatch;
    a wristband; and
    a skin patch.

4. The metabolic physical activity monitor of claim 3, wherein said at least one sensor is removeably attached to the body-worn base.

5. The metabolic physical activity monitor of claim 2, wherein said at least one sensor comprises:
    a single sensor.

6. The metabolic physical activity monitor of claim 5, wherein said at least one sensor is one of:
    single-use; and
    reusable.

7. The metabolic physical activity monitor of claim 1, wherein the at least one body fluid comprises one of:
    sweat;
    saliva; and
    tears.

8. The metabolic physical activity monitor of claim 1, wherein said image capturer captures sensor readings; and
    wherein said image capturer comprises at least one of:
        a photometer;
        a smart watch with optical reader; and
        a digital camera.

9. The metabolic physical activity monitor of claim 3, wherein:
    at least one signal detector and at least one transmitter are integrated as at least one transceiver.

10. The metabolic physical activity monitor of claim 9, wherein said at least one transceiver is mounted on said base.

11. The metabolic physical activity monitor of claim 10, wherein said at least one transceiver is disposed on said base such that each of said at least one transceiver makes direct contact with a corresponding one of said at least one skin sensor.

* * * * *